(12) United States Patent
Hoshi et al.

(10) Patent No.: US 8,921,038 B2
(45) Date of Patent: Dec. 30, 2014

(54) METHOD FOR EVALUATING REGENERATED CARTILAGE

(71) Applicants: Kazuto Hoshi, Bunkyo-ku (JP);
Tsuyoshi Takato, Bunkyo-ku (JP);
Motohiro Harai, Yokohama (JP)

(72) Inventors: Kazuto Hoshi, Bunkyo-ku (JP);
Tsuyoshi Takato, Bunkyo-ku (JP);
Motohiro Harai, Yokohama (JP)

(73) Assignees: Fujisoft Incorporated, Yokohama-shi (JP); The University of Tokyo, Tokyo (JP)

( * ) Notice: Subject to any disclaimer, the term of this patent is extended or adjusted under 35 U.S.C. 154(b) by 0 days.

(21) Appl. No.: 13/946,497

(22) Filed: Jul. 19, 2013

(65) Prior Publication Data
US 2013/0302834 A1    Nov. 14, 2013

Related U.S. Application Data

(63) Continuation of application No. PCT/JP2012/050811, filed on Jan. 17, 2012.

(30) Foreign Application Priority Data

Jan. 19, 2011 (JP) ................................. 2011-009253

(51) Int. Cl.
| | |
|---|---|
| C12Q 1/00 | (2006.01) |
| G01N 33/68 | (2006.01) |
| G01N 33/50 | (2006.01) |
| C12N 5/077 | (2010.01) |
| A61L 27/18 | (2006.01) |
| A61L 27/38 | (2006.01) |
| A61L 27/56 | (2006.01) |

(52) U.S. Cl.
CPC ............ *G01N 33/68* (2013.01); *G01N 33/5005* (2013.01); *G01N 33/6887* (2013.01); *C12N 5/0655* (2013.01); *A61L 27/18* (2013.01); *A61L 27/3817* (2013.01); *A61L 27/3852* (2013.01); *A61L 27/3895* (2013.01); *A61L 27/56* (2013.01); *C12N 2501/115* (2013.01); *C12N 2501/33* (2013.01); *C12N 2533/40* (2013.01); *G01N 2333/78* (2013.01); *G01N 2800/245* (2013.01)
USPC ................................................ 435/4; 436/86

(58) Field of Classification Search
None
See application file for complete search history.

(56) References Cited

U.S. PATENT DOCUMENTS

| | | | |
|---|---|---|---|
| 7,319,035 B2 * | 1/2008 | Vacanti et al. | ................ 435/366 |
| 2006/0228423 A1 * | 10/2006 | Yanaga et al. | ................ 424/572 |
| 2007/0134793 A1 | 6/2007 | Hoshi et al. | |
| 2008/0226611 A1 * | 9/2008 | Noh et al. | ................. 424/93.21 |

FOREIGN PATENT DOCUMENTS

| | | |
|---|---|---|
| CN | 1010014699 | 8/2007 |
| WO | 2006/022263 | 3/2006 |

OTHER PUBLICATIONS

Takahashi, T., Ogasawara, T., Asawa, Y., Mori, Y., Uchinuma, E., Takato, T., and Hoshi, K. "Three-Dimensional Microenvironments Retain Chondrocyte Phenotypes During Proliferation Culture", Tissue Engineering 2007, vol. 13, pp. 1583-1592.*
Santos, G.C., Carvalho, K.C., Falzoni, R., Simoes, A.C.Q., Rocha, R.M., Lopes, A., Vassallo, J., Reis, L.F.L., Soares, F.A., and da Cunha, I.W. "Glial fibrillary acidic protein in tumor types with cartilaginous differentiation", Modern Pathology 2009, vol. 22, pp. 1321-1327.*
International Search Report issued Feb. 28, 2012 in PCT/JP2012/050811 filed Jan. 17, 2012.
Vira Kasantikul, et al., "Positivity to Glial Fibrillary Acidic Protein in Bone, Cartilage, and Chordoma", Journal of Surgical Oncology 41:22-26 (1989).
Wan-Ju Li, et al., "Evaluation of articular cartilage repair using biodegradable nanofibrous scaffolds in a swine model: a pilot study", Journal of Tissue Engineering and Regenerative Medicine, J. Tissue Eng Regen med 2009; 3: 1-10.
Mats Brittberg, M.D., et al., "Treatment of Deep Cartilage Defects in the knee with autologous Chondrocyte Transplantation" The New England Journal of Medicine, vol. 331, Oct. 6, 1994, No. 14.
Hiroko Yanaga, M.D., et al., "Clinical Application of Cultured Autolgous Human Auricular Chondrocytes with Autologous Serum for Craniofacial or Nasal Augmentation and Repair", www.plastreconsurg.org, Dec. 31, 2004, pp. 219-229.
Combined Office Action and Search Report issued Jul. 26, 2013 in Taiwanese Application No. 101102243 (With English Translation).
International Preliminary Report on Patentability and Written Opinion issued Aug. 1, 2013 in Application No. PCT/JP2012/050811 (English Translation).
S. Wislet-Gendebien, et al., "Regulation of neural markers nestin and GFAP expression by cultivated bone marrow stromal cells", Journal of Cell Science, vol. 116, 2003, pp. 3295-3302.

* cited by examiner

*Primary Examiner* — Allison Fox
*Assistant Examiner* — Michelle F Paguio Frising
(74) *Attorney, Agent, or Firm* — Oblon, Spivak, McClelland, Maier & Neustadt, L.L.P.

(57) ABSTRACT

A method, according to an embodiment, for evaluating a regenerated cartilage includes allowing a group of cells containing auricular chondrocytes to stand in the presence of a culture medium, subsequently collecting at least a portion of a liquid component from the culture medium, measuring the GFAP content of the collected liquid component, and determining whether a regenerated cartilage that has been obtained or can be obtained from the group of cells is suitable for transplantation based on the GFAP content.

8 Claims, 6 Drawing Sheets

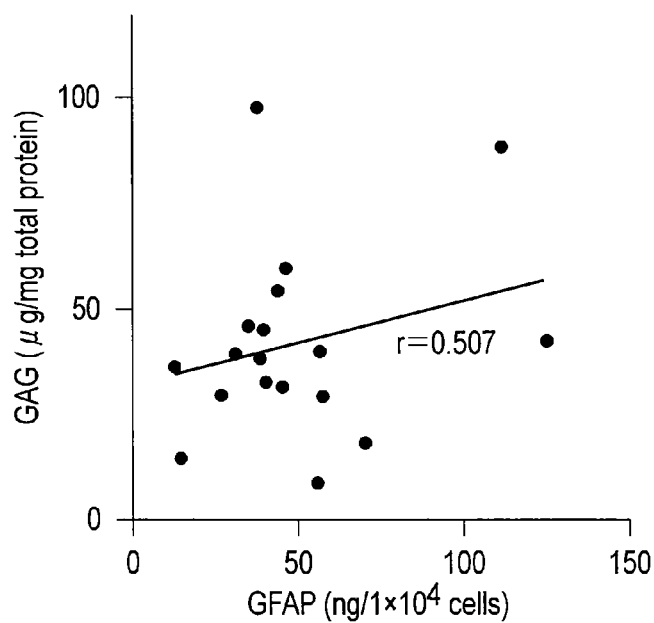
F I G. 3
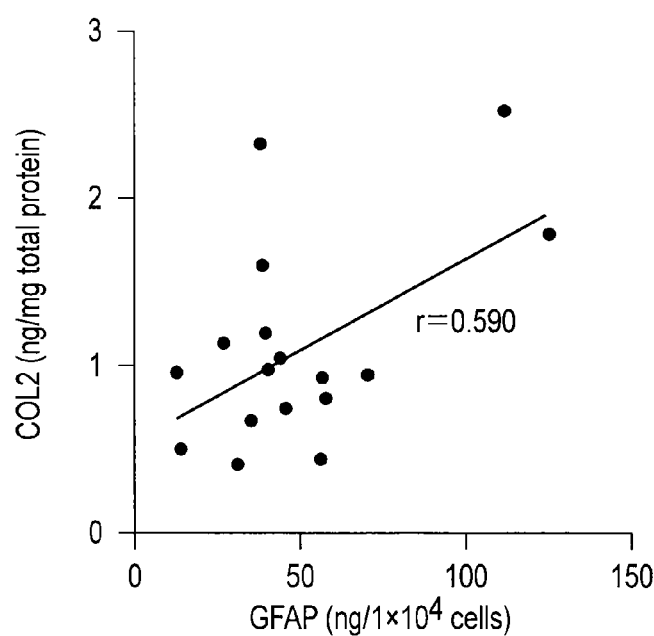
F I G. 4

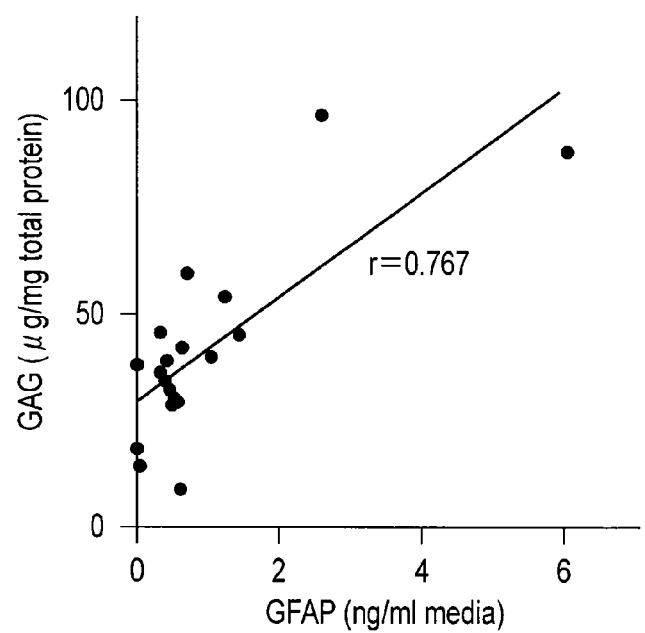
F I G. 5
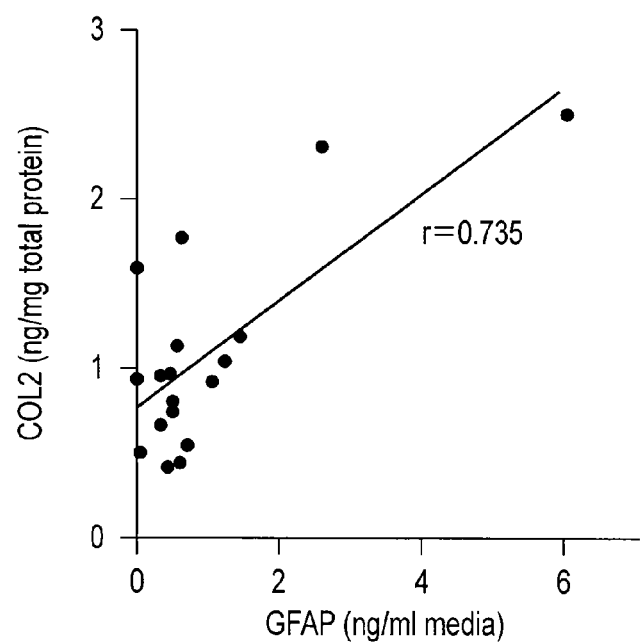
F I G. 6

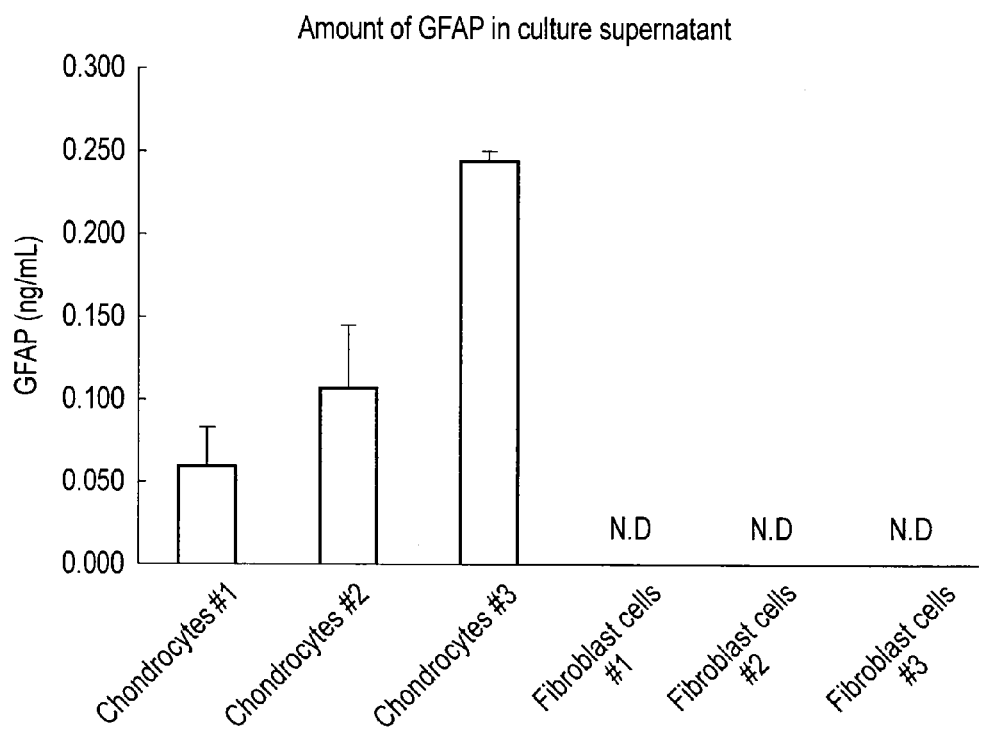
F I G. 7

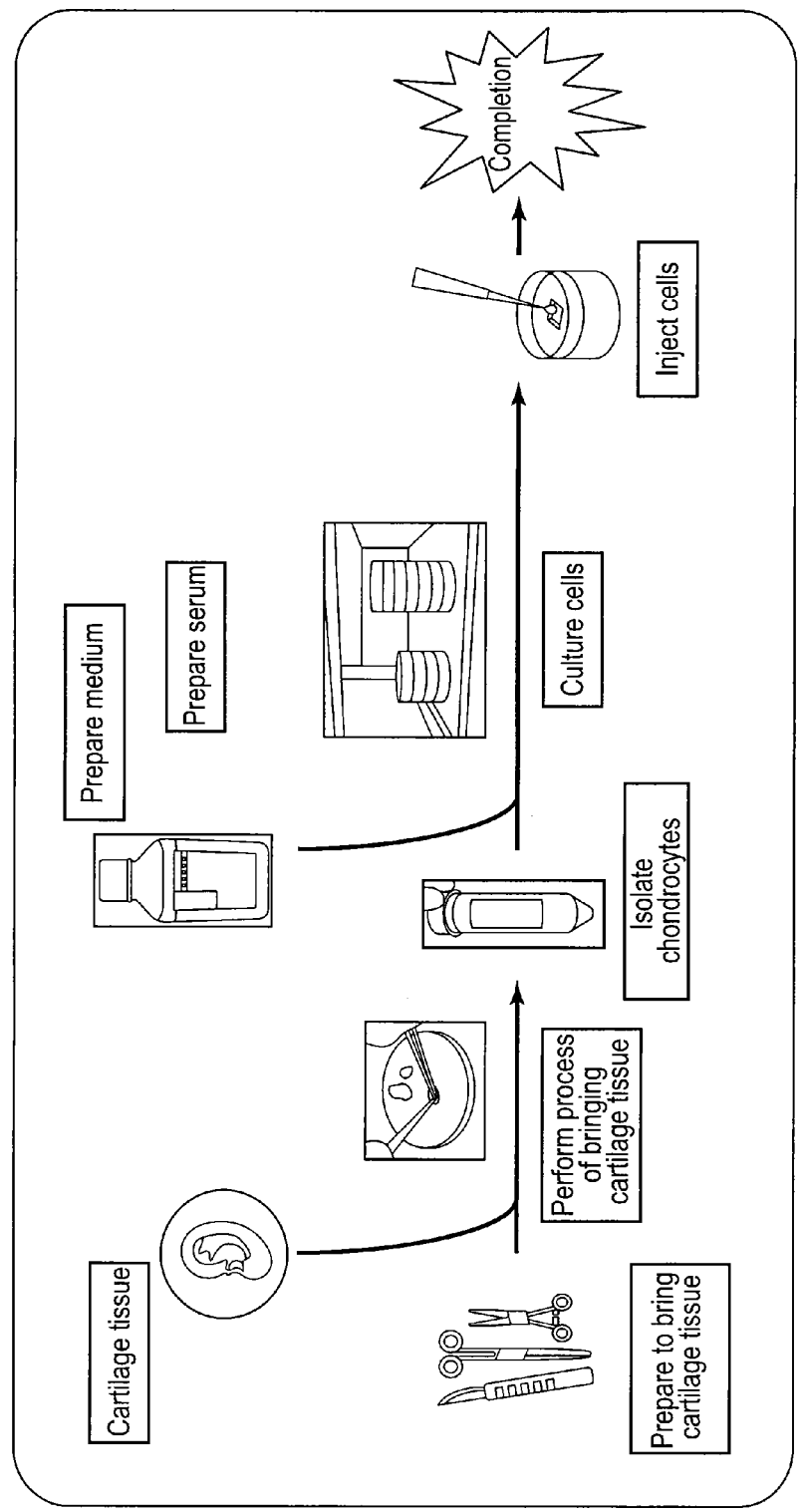
F I G. 14

METHOD FOR EVALUATING REGENERATED CARTILAGE

CROSS REFERENCE TO RELATED APPLICATIONS

This application is a Continuation application of PCT Application No. PCT/JP2012/050811, filed Jan. 17, 2012 and based upon and claiming the benefit of priority from prior Japanese Patent Application No. 2011-009253, filed Jan. 19, 2011, the entire contents of all of which are incorporated herein by reference.

BACKGROUND OF THE INVENTION

1. Field of the Invention

The present invention relates to a method for evaluating a regenerated cartilage.

2. Description of the Related Art

Concerning congenital morphological abnormalities in the maxillofacial region or maxillofacial defects after malignant tumor excision, tissue restoration and reconstruction surgeries have been performed by the autologous implantation. However, problems such as the limitation of the size of the tissue which can be collected and the invasion of the site to be transplanted have remained in the autogenous implantation. Particularly, clinical application of cartilage tissue engineering is relatively progressed. Currently, autologous chondrocyte implantation (ACI) is widely spread. Swedish researchers first reported the original method of ACI in 1995. The original method of ACI is a method comprising injecting autogenously-cultured chondrocytes into the local defect of articular cartilage due to athletic injury as a cell suspension and covering the defect with a periosteal patch in order to prevent leakage.

Concerning defects and abnormalities in the maxillofacial region, cases of regenerative surgery, such as augmentation rhinoplasty by the silicone implant as well as applications where a suspension of autologous chondrocytes was injected into the saddle nose have been reported.

For example, gene expression and surface markers have been used for the evaluation of the characteristics of the cultured chondrocytes. However, these markers are lack of quantitative performance. Thus, it is currently necessary to sacrifice a part of a group of cells which is intended to be finally obtained.

The technologies related to such technologies are described in, for example, the following references.

Brittberg M, Lindahl A, Nilsson A, Ohlsson C, Isaksson O, Peterson L. 1994. Treatment of deep cartilage defect in the knee with autologous chondrocytes transplantation. N Engl J Med 331(14):889-895.

Yanaga H, Yanaga K, Imai K, Koga M, Soejima C, Ohmori K. 2006. Clinical application of cultured autologous human auricular chondrocytes with autologous serum for craniofacial or nasal augmentation and repair. Plast Reconstr Surg 117(6):2019-2030.

BRIEF SUMMARY OF THE INVENTION

Technical Problem

An object of the present invention is to provide a method for quantitatively evaluating a regenerated cartilage without sacrificing some of the chondrocytes which are used as the regenerated cartilage or its material.

Solution to Problem

According to an embodiment of the present invention, there is provided a method for evaluating a regenerated cartilage comprising: allowing a group of cells containing auricular chondrocytes to stand in the presence of a culture medium; subsequently collecting at least a portion of a liquid component from the culture medium; measuring the GFAP content of the collected liquid component; and determining whether a regenerated cartilage that has been obtained or can be obtained from the group of cells is suitable for transplantation based on the GFAP content.

BRIEF DESCRIPTION OF THE SEVERAL VIEWS OF THE DRAWING

FIG. 3 is a view illustrating results in which a correlation between the GAG and GFAP produced by human auricular chondrocytes has been evaluated using cultured human auricular chondrocytes.

FIG. 4 is a view illustrating results in which a correlation between the COL2 and GFAP produced by human auricular chondrocytes has been evaluated using cultured human auricular chondrocytes.

FIG. 5 is a view illustrating results in which a correlation between the GAG and GFAP produced by human auricular chondrocytes has been evaluated using a culture supernatant obtained by culturing human auricular chondrocytes.

FIG. 6 is a view illustrating results in which a correlation between the COL2 and GFAP produced by cultured human auricular chondrocytes has been evaluated using a culture supernatant obtained by culturing human auricular chondrocytes.

FIG. 7 is a view illustrating measurement results of the amount of GFAP in a culture supernatant obtained by culturing chondrocytes and fibroblast cells respectively.

FIG. 14 is a view schematically illustrating a process of producing a regenerated product of an auricular cartilage according to one embodiment.

DETAILED DESCRIPTION OF THE INVENTION

1. Summary

Figure 1:
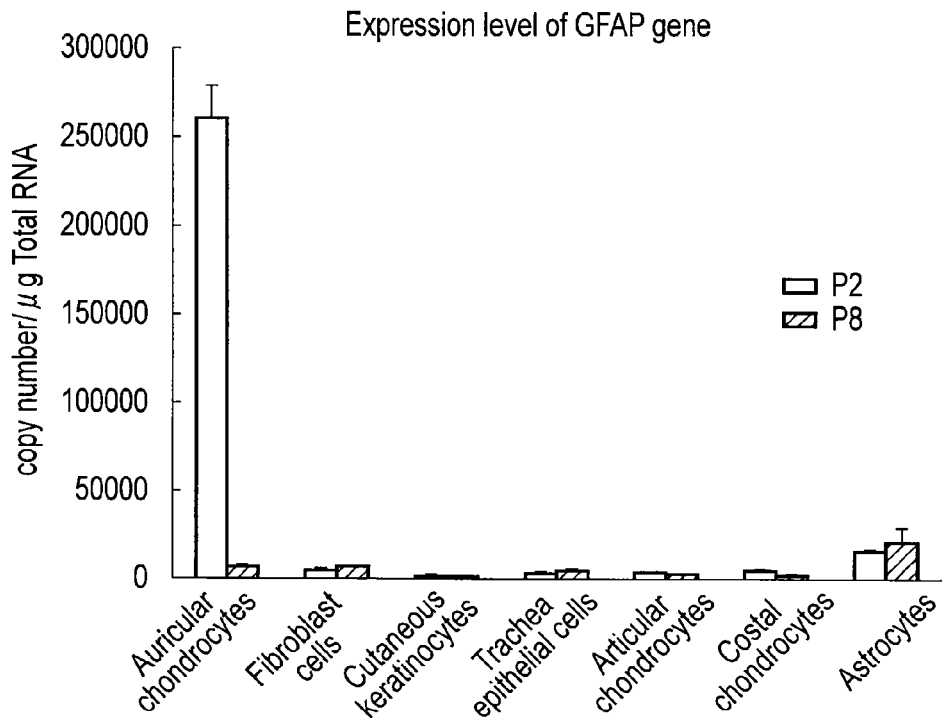
FIG. 1 is a view illustrating expression levels of GFAP genes in various cells.

Conventionally, a method for injecting chondrocytes has been done as the tissue engineering for cartilage reconstruction.

However, the chondrocytes themselves do not have a sufficient size and strength. Accordingly, there is still a high possibility that the purpose of tissue reconstruction cannot be sufficiently achieved by only the method for injecting chondrocytes. Under such circumstances, the present inventors have developed a means for providing a regenerated cartilage like an "implant" having a sufficient size and strength. In the development, they have focused on that when the chondrocytes are transplanted into the body, a certain quality is required to be guaranteed. Specifically, the quality means that the regenerated cartilage has cartilage characteristics. The term "cartilage characteristics" herein is used interchangeably with the terms such as "characteristics as cartilage", "characteristics of cartilage", "properties as cartilage", and "properties of cartilage". The term "cartilage characteristics" means specific properties as the cartilage suitable for transplantation. Specifically, it means properties in which safe transplantation can be performed, cartilage is formed after transplantation, the cartilage can engraft in the body. According to an example, the term "cartilage characteristics" means properties in which strong cartilage regeneration in the body is exhibited after transplantation. Further, the term "cartilage characteristics" may be interpreted as appropriateness for transplantation. In order to allow the regenerated cartilage to include cartilage characteristics, it is necessary that there is no contamination of foreign substances such as other cells and no overgrowth.

The chondrocytes are important constituent elements which secrete a cartilage matrix that influences the characteristics and function of regenerated cartilage. For example, when chondrocytes are overgrown, the cells are dedifferentiated and the cartilage characteristics are reduced. Further, the cartilage characteristics are lost. When fibroblast cells come to be mixed in isolated cells at the time of isolating chondrocytes and the fibroblast cells are overgrown during culture, there is a production risk of expulsion of desired chondrocytes. When the cultured tissue in which the chondrocytes have been expelled by the fibroblast cells is transplanted, the fibroblast cells are transplanted in place of the chondrocytes. Such a transplanted tissue cannot engraft as cartilage. Therefore, prior to transplantation, it is mandatory to determine in advance that tissue engineered cartilage product does not contain other cells in an amount that expels the chondrocytes, contains the chondrocytes in a sufficient amount, does not overgrow after transplantation, and can maintain cartilage characteristics.

The present inventors have found a specific marker which is an indicator illustrating whether a regenerated cartilage that can be obtained or has been obtained using a cell group containing chondrocytes, particularly auricular chondrocytes, is suitable for transplantation. The present invention is based on this finding. According to the marker, cartilage characteristics of the regenerated cartilage that can be obtained or has been obtained using the cell group can be quantitatively evaluated without sacrificing the desired product which is intended to be finally obtained.

2. Marker Specific to Auricular Chondrocytes

A marker specific to the above chondrocytes, particularly auricular chondrocytes is a glial fibrillary acidic protein (GFAP)).

GFAP is a protein which is specifically localized, generally in the nervous system such as astrocytes or Schwann cells.

The present inventors have found that GFAP is expressed specifically and highly in cultured auricular chondrocytes which are a cell source useful for cartilage tissue engineering, and the expression level of the GFAP gene and the amount of GFAP protein are gradually reduced by subculture.

The reduced cartilage characteristics caused by contamination of other cells such as fibroblast cells as well as overgrowth of auricular chondrocytes can be detected by quantifying the amount of the GFAP protein. Accordingly, there is provided a method for evaluating cartilage characteristics of tissue engineered cartilage product.

According to an embodiment of the present invention, there is provided a method for evaluating a regenerated cartilage comprising: allowing a group of cells containing auricular chondrocytes to stand in the presence of a culture medium; subsequently separating at least a portion of a liquid component from the culture medium; measuring the GFAP content of the separated liquid component; and determining whether a regenerated cartilage that can be obtained from the group of cells is suitable for transplantation based on the GFAP content.

In the method, quantitative information about the cartilage matrix accumulation can be obtained by measuring the amount of a liquid component (e.g., the amount of GFAP contained in a culture supernatant).

The term "cartilage matrix" herein means a generic term for substances forming the basis of cartilaginous structures. The cartilage matrix is, for example, glycosaminoglycan (GAG) or type II collagen (COL2).

As illustrated in the examples described below, in the study on which the present invention is based, it has been newly found that the GFAP content of the culture supernatant correlates with the accumulation of GAG and COL2. Based on the knowledge, the evaluation of the cartilage characteristics has been achieved by measuring the amount of a liquid component (e.g., the amount of GFAP contained in a culture supernatant).

Regarding human articular chondrocytes which are used for production of a regenerated cartilage, examples of markers which enhance the expression of the cells include CD10, CD26, CD44, CD49c, CD81, and CD166. Examples of markers which decrease the expression of the cells include CD94a and CD106. They are cell adhesion molecules and are used as cell surface markers. The cell surface markers are analyzed by flow cytometry, and thus it is difficult to quantitatively compare the different systems analyzed separately. The state of the markers may change depending on the culture environment such as the adhesion state of the cells, and thus it is also difficult to establish certain standards.

In addition to the cell adhesion molecules, serine protease inhibitors (Serpin) A1 and A3, fibroblast growth factor-18 (FGF-18), melanoma inhibitory activity factor (MIA), and the like have been confirmed. Particularly, FGF-18 is a factor whose gene expression level is increased by repeating plane culture, and thus there is a possibility that it can be used as an indicator of capacity to produce a cellular matrix of chondrocytes. However, when these factors are used as indicators, they are evaluated at the genetic level. Thus, problems remain in quantitative performance. All of these factors are secretory proteins. The amount of physiologically active substances secreted from proliferating cultured chondrocytes is expected to be very low. Although there is a possibility that a culture supernatant is used as a sample and the amount of proteins contained in the sample can be measured, it is difficult to detect them. For these reasons, GFAP was employed as the indicator.

The expression level of GFAP in articular chondrocytes is lower than that of auricular chondrocytes and changes in the expression level of GFAP due to subculture are small. Accordingly, auricular chondrocytes are used as a source of regenerated cartilage.

For the above reasons, it is clear that the evaluation method according to one embodiment in which auricular chondrocytes are used as the source of regenerated cartilage and GFAP is used as an indicator of the cartilage characteristics of the regenerated cartilage is advantageous.

3. Chondrocytes

Chondrocytes used herein are auricular chondrocytes.

A source of chondrocytes may be any mammal. Examples of mammals include mice, rats, rabbits, dogs, cats, horses, cows, monkeys, and humans. Preferable examples are humans.

The choice of mammal as the source of chondrocytes is dependent on the mammal to which the regenerated cartilage formed by chondrocytes is transplanted. The regenerated cartilage formed by chondrocytes will be described below.

When humans are subject for transplantation, auricular chondrocytes derived from humans (hereinafter referred to as "human auricular chondrocytes"), more preferably autologous auricular chondrocytes derived from humans are used. Here, the term "autologous auricular chondrocytes" means cells collected from a subject to which the regenerated cartilage formed by chondrocytes is transplanted in advance of the transplantation and production of regenerated cartilage.

The chondrocytes are isolated, for example, in the following manner. First, a cartilage fragment is surgically collected from a mammal as a donor. Next, the collected cartilage fragment is finely cut under aseptic conditions, followed by digestion with desired digestive enzymes such as collagenase and/or gelatinase, trypsin, pepsin, and aggrecanase, if necessary. As a result, a cell group is obtained, the cell group contains a population of cells containing the chondrocytes individually released and/or a piece of fine fragmented tissue formed by a plurality of chondrocytes bound each other in at least a part thereof.

4. Culture of Chondrocytes

Subsequently, a group of cells containing auricular chondrocytes is allowed to stand in the presence of a medium.

Here, the medium may be one which causes cell division or one which does not cause cell division. For example, the medium is a buffer which contains a component necessary for survival of the group of cells.

The term "allowing a group of cells to stand" means a process of maintaining the cells under specific conditions. In the maintaining process, cell division typically occurs. Namely, the process of allowing a group of cells to stand may be a culturing process. Further, in the maintaining process, the cell division may not occur. For example, when the number of living cells required for production of regenerated cartilage has been already obtained, the cell division may not occur in the maintaining process. When the cell division occurs in the maintaining process under specific conditions (namely, when the culture is performed), the culturing method may be any method known to those skilled in the art as long as the number of living chondrocytes required for production of regenerated cartilage can be obtained. The culturing method may be, for example, a subculturing process in order to obtain the required number of living cells. According to an example, subculture is performed by culturing the isolated chondrocytes for 3 weeks based on plane culture, subculturing them once, and further culturing them for 3 weeks to increase by about 1000-fold. Further, another subculturing process may be performed. The style of culture is not particularly limited and can be appropriately selected depending on the purpose. Examples of the style of culture include suspension culture in a bottle, plane and/or suspension culture in a culture dish (monolayer culture), pellet culture, and three-dimensional culture with hydrogels.

The medium to be used is a medium suitable for cultivation of chondrocytes known in themselves. The medium is preferably a DMEM medium, an MEM medium, a DMEM/F12 medium or a serum containing DMEM/F12 medium. The amount of the medium is from 20 to 20,000 mL based on a 1 mL volume of a cell group containing chondrocytes.

The cell group is allowed to stand, for example, in the presence of 3 to 7% of $CO_2$ at a humidity of 80 to 100% at a temperature of 36 to 38° C. For example, when culture is performed, the time for allowing the cell group to stand is the time required for the culture. Further, the medium may or may not be stirred during allowing the cell group to stand. Preferably, the medium is stirred.

The cell group containing chondrocytes after being allowed to stand is bound to each other. The cell group may form, at least partially, a tissue, or it may be an individually released chondrocyte. Further, the cell group containing chondrocytes may be a primary culture and/or subculture.

The survival ratio of the chondrocytes contained in the cell group, namely, the proportion of cartilage living cells of the chondrocytes contained in the cell group is preferably 80% or more. If the survival ratio of the chondrocytes is less than 80%, the regeneration of healthy cartilage may not be expected. The method for measuring the survival ratio is any method known in itself. The method for measuring the survival ratio is, for example, the PE measurement method using a Nucleocounter.

The cell group containing chondrocytes contains, for example, 240 million or more of cartilage living cells. Such a cell group contains the number of cartilage living cells required for the production of regenerated cartilage. The regenerated cartilage can be produced by using the cell group.

5. Measurement of Amount of GFAP

Subsequently, at least a portion of a liquid component is collected from the above culture medium.

Here, the liquid component can be obtained by removing at least cells from the culture medium. The culture medium may be a medium during culture or may be a buffer obtained by temporarily replacing the medium with a buffer with a physiological composition known in itself in the middle of culture and incubating for a predetermined period of time. The liquid component, for example, is a culture supernatant.

As a method for collecting a liquid component from a culture medium, any method for obtaining a medium from the culture medium so as not to contain a cell group is used. For example, as the method for collecting a liquid component from a culture medium, a centrifugation method is used.

The period to collect the liquid component from the culture medium may be at least one period selected from the followings: after isolation of the cell group containing chondrocytes, before culture, during culture, after culture, at the end of culture during primary culture, before subculture, after subculture, during subculture, before formation of regenerated cartilage, after formation of regenerated cartilage, before transplantation of regenerated cartilage, after transplantation of regenerated cartilage. For example, the cell group is suspended in a buffer immediately after isolation of the cell group containing chondrocytes, and then the liquid component of the obtained suspension is collected. When the liquid component is collected immediately after isolation and is subjected to the method for measuring the amount of GFAP, it is possible to examine the purity of chondrocytes in the isolated cell group. The liquid component is collected immediately after isolation of the cell population and, for example, during culture and/or after formation of regenerated cartilage or immediately before transplantation. Then, the component may be subjected to the following measurement. When the liquid component is collected immediately before transplantation and is subjected to the measurement method, it is possible to control the quality of regenerated cartilage.

Subsequently, the GFAP content of the liquid component thus separated is measured. The method for measuring the GFAP content may be any method known in itself, which can measure the amount of GFAP. For example, the method for measuring the GFAP content is ELISA, PR-PCR or western blotting.

Subsequently, it is determined whether a regenerated cartilage that can be obtained or has been obtained from the group of cells is suitable for transplantation based on the thus measured GFAP content. For example, when the GFAP content of the liquid component is 0.05 ng or more per 1 mL of the liquid component, the regenerated cartilage that can be obtained or has been obtained from the group of cells is determined to be suitable for transplantation. Preferably, when the GFAP content of the liquid component is 0.5 ng or more per 1 mL of the liquid component, the regenerated cartilage that can be obtained or has been obtained from the group of cells is determined to be suitable for transplantation. More preferably, when the GFAP content of the liquid component is 5 ng or more per 1 mL of the liquid component, the regenerated cartilage that can be obtained or has been obtained from the group of cells is determined to be suitable for transplantation.

If the GFAP content of the liquid component is 0.05 ng or more per 1 mL of the liquid component, the regenerated cartilage that can be obtained or has been obtained from the group of cells engraft as cartilage after transplantation. Preferably, strong cartilage regeneration is exhibited. On the other hand, when the GFAP content is less than 0.05 ng per 1 mL of the liquid component, there is a high possibility that the regenerated cartilage that can be obtained from the group of cells does not engraft as cartilage after transplantation or desired cartilage regeneration is not exhibited.

The cell group that has been determined to be suitable for transplantation is then used for the formation of regenerated cartilage as described below. On the other hand, the cell group that has been determined to be unsuitable for transplantation is not used for the formation of regenerated cartilage.

Even if the regenerated cartilage has been subjected to the above evaluation, when the regenerated cartilage has been determined to be unsuitable for transplantation, the regenerated cartilage is not used for transplantation.

6. Formation of Regenerated Cartilage

The regenerated cartilage is formed using a cell group containing the chondrocytes which have been left in the presence of a medium. The cell group used herein is a group cell in which a regenerated cartilage that can be obtained from the group of cells has been determined to be suitable for transplantation based on the GFAP content.

For example, the regenerated cartilage is formed by three-dimensionally culturing a cell group containing chondrocytes. The three-dimensional culture is performed using a scaffold material. Specifically, the three-dimensional culture is performed by culturing chondrocytes on or in the scaffold material. The material, property, shape, structure, and size of the scaffold material to be used are not limited. They can be appropriately selected depending on the purpose.

Examples of the scaffold material include atelocollagen, fibrin, hyaluronic acid, and a biodegradable polymer porous material. Examples of the biodegradable polymer porous material include PLLA, PGA, and PLGA. The scaffold material may be formed using any known method. The three-dimensional culture may be performed further using a gelator. For example, stable three-dimensional culture is performed by mixing a gelator and a cell group containing chondrocytes and bringing the mixture into contact with a scaffold material and thus a stable regenerated cartilage can be obtained. Examples of the gelator include atelocollagen and alginate. The three-dimensional culture is performed, for example, under the conditions (at 37° C. in a 5% $CO_2$ incubator for 2 hours).

As described above, the regenerated cartilage suitable for transplantation is produced.

The regenerated cartilage thus produced has a certain size, and it can be preferably used as an implant. The regenerated cartilage may be in suspension or solid form. Preferably, it is in solid form.

For example, the regenerated cartilage produced can be used as a transplantation material for medical purpose in order to supplement or reinforce the cartilage defect or the site of cartilage injury. It can be used as the transplantation material for medical purpose, particularly, congenital morphological abnormalities such as nose deformity due to cleft lip and palate. The regenerated cartilage can be used as a transplant material for cosmetic surgery.

The cartilage tissue engineering mainly includes four processes: (1) collection of cartilage from patients; (2) isolation and culture of chondrocytes; (3) harvest of cultured chondrocytes or formation of regenerated cartilage; and (4) transplantation to patients. The second process (the isolation and culture of chondrocytes) is an essential part for production of tissue-engineered medical products which is performed in a special laboratory called "Cell Processing Center". Therefore, it is a process required for the tightest quality control.

Conventionally, there have been problems such that the quality of regenerated cartilage is not guaranteed due to the contamination of other cells except chondrocytes or overgrowth of chondrocytes, it is impossible to provide the planned medical treatment to patients or the formation of cartilage is reduced after transplantation. The contamination of other cells could not be determined because an indicator of the purity of chondrocytes was not established. Other cells prevent the growth of chondrocytes and the differentiation of the cell population to cartilage. Further, in the overgrow of chondrocytes, the dedifferentiation of the cell population cultured is significantly progressed, which results in reduced cartilage characteristics. The overgrowth has been caused because it is difficult to accurately measure the number of chondrocytes at the time of isolation. In other words, the number of chondrocytes at the time of isolation has been overestimated and the target cell number has been obtained by subculture. As a result, the overgrowth of the chondrocytes has been caused.

According to the method for evaluating a regenerated cartilage, it is possible to evaluate cartilage characteristics of a regenerated cartilage that has been obtained or can be obtained from cultured chondrocytes. Thus, the conventional problems can be solved. Specifically, in the evaluation method, a quantitative indicator of the purity of chondrocytes in the cell group can be provided by measuring the GFAP content. Accordingly, it is possible to exclude the cell group which contains other cells in an amount that expels the chondrocytes. Since it is determined whether the regenerated cartilage which is produced using a cell group containing chondrocytes is suitable for transplantation, it is possible to avoid a circumstance where the formation of cartilage in the body is reduced after transplantation.

In the evaluation of cartilage characteristics, the cell group containing chondrocytes is not used, but a liquid component which is separated from a culture medium and does not contain chondrocytes, namely, for example, a culture supernatant is used. Thus, this is very advantageous for the production of regenerated cartilage in terms that cells which are precious raw materials for tissue engineered cartilage products are not impaired.

Further, the quality of the regenerated cartilage produced using the method for evaluating cartilage characteristics is guaranteed. Thus, the regenerated cartilage can be safely used as a transplantation material for medical and cosmetic purposes.

EXAMPLES

Hereinafter, examples of the present invention will be described.

Example 1

Example 1. Examination of an indicator for determining that cells forming a tissue engineered cartilage product are auricular chondrocytes Genes highly expressed in auricular chondrocytes increased by 1000-fold after culturing, which were used for the production of a tissue engineered cartilage product, were searched in the following manner.

Auricular chondrocytes, fibroblast cells, cutaneous keratinocytes, trachea epithelial cells, articular chondrocytes, costal chondrocytes, and astrocytes (astroglial cells) were subcultured by the monolayer culture method about once per week, followed by serial subculturing for a long period. At the time of the second passage (PS) and the eighth passage (P8), Total RNAs were collected from each of the cultured cells. Genes high-expressed in the cells were searched by a microarray method using GeneChip (registered trademark) Human Genome U133 plus Array, manufactured by Affymetrix.

As a result, genes such as fibroblast growth factor (FGF)-18 and glial fibrillary acidic protein (GFAP) were detected. In the genes, particularly the gene with a high expression level was the GFAP gene.

Further, the expression level of the GFAP gene was measured by the Real Time PT-PCR assay. Three samples for each cell were measured, and then an average of the measured values and a standard deviation thereof were obtained.

The results of the cells are illustrated in FIG. 1.

As is clear from FIG. 1, a significantly high expression level of GFAP was observed in auricular chondrocytes, among auricular chondrocytes, fibroblast cells, cutaneous keratinocytes, trachea epithelial cells, articular chondrocytes, costal chondrocytes, and astrocytes.

The result suggested that the detection of GFAP allows for the exclusion of a risk such that the auricular chondrocytes are expelled by the fibroblast cells during culture and the fibroblast cells are unintentionally administered.

Example 2

Examination of the Suitability as an Indicator of Production of a Cartilage Matrix of GFAP Gene Auricular chondrocytes from 6 different origins were subcultured in a DMEM/F12 culture solution containing 5% serum, FGF-2, and insulin about once a week. The resultant cells were serially subcultured by the monolayer culture method for a long period up to the eighth passage (P8). When the auricular chondrocytes were increased by about 100-fold after culture (P2) (abundant amount of matrix production) and the cells were increased by about 100 million-fold (P8), Total RNAs were collected from the cultured cells. The expression level of the GFAP gene was measured by the Real Time PT-PCR assay.

Figure 2:
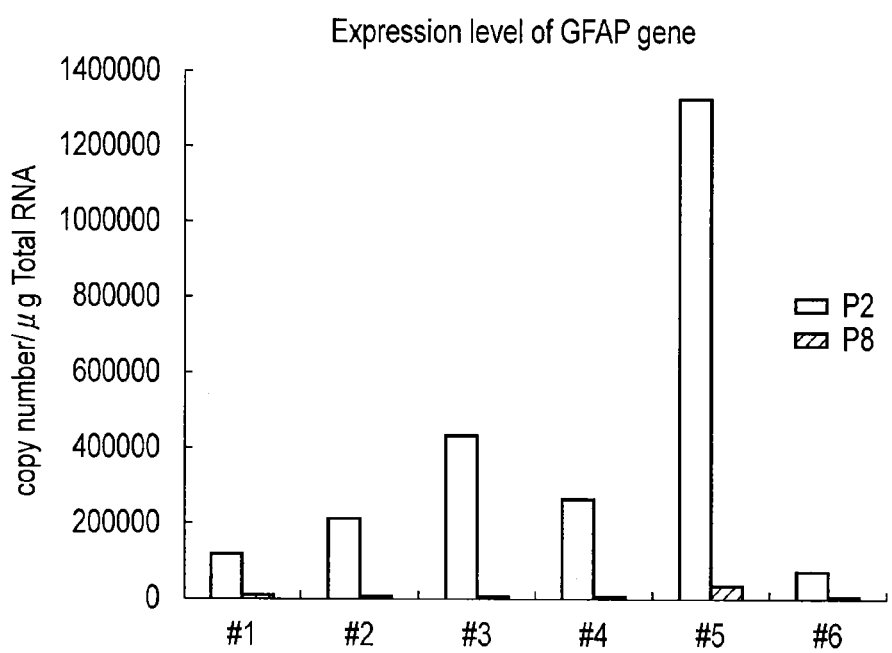
FIG. 2 is a view illustrating expression levels of GFAP genes in human auricular chondrocytes of different origins.
Figure 8:
FIG. 8 is a view illustrating an image of regenerated tissue after transplantation of the cultured chondrocytes #1 (illustrated in FIG. 7).
Figure 11:
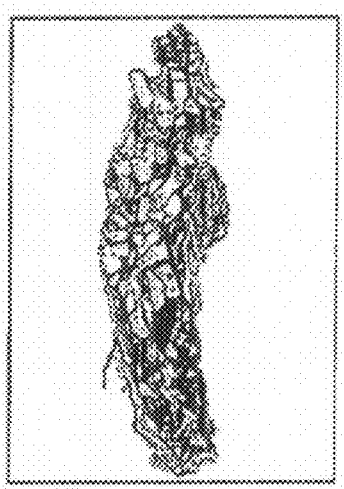
FIG. 11 is a view illustrating an image of regenerated tissue after transplantation of the cultured fibroblast cells #1 (illustrated in FIG. 7).
Figure 9:
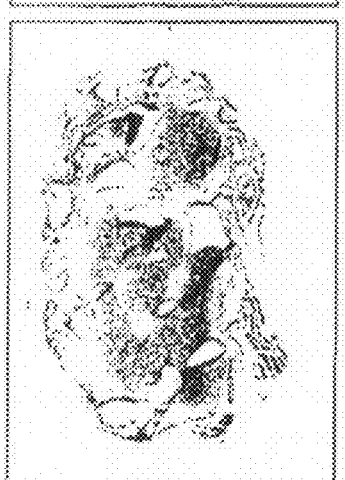
FIG. 9 is a view illustrating an image of regenerated tissue after transplantation of the cultured chondrocytes #2 (illustrated in FIG. 7).
Figure 12:
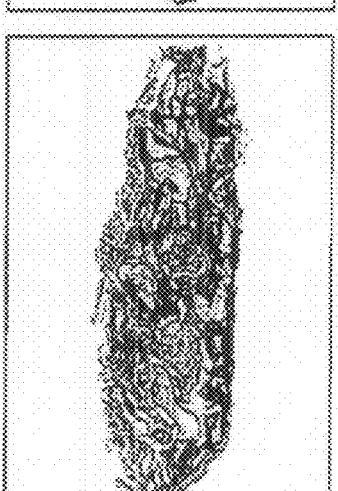
FIG. 12 is a view illustrating an image of regenerated tissue after transplantation of the cultured fibroblast cells #2 (illustrated in FIG. 7).
Figure 10:
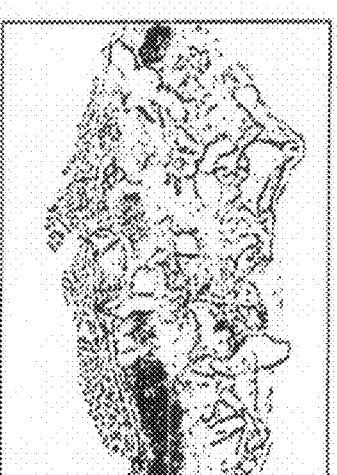
FIG. 10 is a view illustrating an image of regenerated tissue after transplantation of the cultured chondrocytes #3 (illustrated in FIG. 7).
Figure 13:
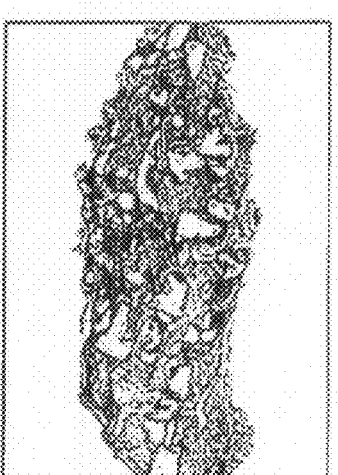
FIG. 13 is a view illustrating an image of regenerated tissue after transplantation of the cultured fibroblast cells #3 (illustrated in FIG. 7).

The results are illustrated in FIG. 2. FIG. 2 suggested that the expression level of P2 was high in all the cases and, as for the gene expression of P2, the copy number was $7.2 \times 10^3$ to $1.321 \times 10^6$ in spite of being cultured under the same culture conditions, and thus very high variations among the cells were illustrated.

In order to reduce the variations in measurements, the evaluation at the protein level was examined.

Example 3

Measurement of GFAP Expression at the Protein Level

Human auricular chondrocytes from 18 different donors were subcultured in a DMEM/F12 culture solution containing 5% serum, FGF-2, and insulin about once a week, followed by long-term culturing up to the third passage. The cultured auricular chondrocytes were trypsinized and harvested, and the cells were mixed in a 1% atelocollagen gel at a concentration of $1 \times 10^7$ cells/mL. 20 µl of the cell-gel mixture was dispensed into a test tube and subjected to a densely embedding culture method in a chondrocyte matrix production inducing medium containing BMP-2/insulin/T3 which contained bone morphogenetic protein (BMP-2 (Bone morphogenetic protein-2)), insulin, and thyroid hormone (T3 (Triiodothryonine)). Three weeks later, the amount of GAG secreted from the chondrocytes and the amount of COL2 were measured by colorimetric and ELISA methods. $1 \times 10^4$ of P3 cultured chondrocytes equal to those embedded in atelocollagen were fractionated, and the amount of GFAP in the cell lysate was measured by the ELISA method. The same test was performed on each of auricular chondrocytes from 18 different donors. The correlation among the amounts of GAG secreted from the cultured cells, the amount of COL2, and the amount of GFAP in the cells was calculated using Excel Statistical Analysis (manufactured by SSRI). The results are illustrated in FIGS. 3 and 4.

FIGS. 3 and 4 suggested that the coefficient of correlation between the amount of GFAP in the cells and the amount of GAG is 0.507, the correlation coefficient with COL2 is 0.590, and there is a moderate correlation between both the values. The result suggested that functional evaluation of the chondrocytes is achieved by measuring GFAP in the chondrocytes forming the regenerated cartilage at the protein level.

Example 4

Examination of Samples for Evaluating the GFAP Content

Auricular chondrocytes from 18 different donors were cultured up to the third passage (P3). The cultured auricular chondrocytes were harvested by trypsinization, and the cells were mixed in a 1% atelocollagen gel at a concentration of $1\times10^7$ cells/mL. 20 μl of the cell-gel mixture was dispensed into a test tube and subjected to a densely embedding culture method in a chondrocyte matrix production inducing medium containing BMP-2/insulin/T3. Three weeks later, the amount of GAG secreted from the chondrocytes and the amount of COL2 were measured by colorimetric and ELISA methods. A portion of the culture supernatant of the P3 cultured chondrocytes equal to those embedded in atelocollagen was fractionated. The GFAP content of the culture supernatant was measured by the ELISA method. The same test was performed on each of auricular chondrocytes from 18 different donors. The correlation among the amounts of GAG secreted from the cultured cells, the amount of COL2, and the amount of GFAP in the culture supernatant was calculated. The results are illustrated in FIGS. 5 and 6.

FIGS. 5 and 6 suggested that the correlation coefficient between the amount of GFAP in the culture supernatant and the amount of GAG is 0.767 and the correlation coefficient between the amount of GFAP in the culture supernatant and the amount of COL2 is 0.735. There is a strong correlation between both the values. As the GFAP content of the culture supernatant is higher, strong cartilage regeneration was exhibited.

Therefore, it was shown that a portion of the culture supernatant is collected and the amount of GFAP is measured by the ELISA method so that the release (shipment) can be determined without impairing cells and tissues.

Example 5

Determination of the Threshold of the Amount of GFAP Protein to Evaluate Cartilage Characteristics Three cases each of cultured auricular chondrocytes at the second passage (P2) and cultured fibroblast cells were cultured in a DMEM/F12 culture solution containing 5% serum, FGF-2, and insulin as a cartilage growth medium for one week. 1 mL of the culture supernatant was fractionated from the culture and then the cultured cells were harvested by trypsinization. The recovered cells were mixed in a 1% atelocollagen gel at a concentration of $1\times10^8$ cells/mL. The resultant mixture was injected to a porous scaffold material, followed by incubation at 37° C. for 2 hours so as to gelatinize the mixture. The gelatinized product was subcutaneously transplanted into the back of nude mice.

Two months later, the transplanted product was removed and cut into half. One of them was used for histological evaluation by toluidine-blue staining. The other was used for quantitative evaluation of proteins for GAG and type II collagen. The GFAP content of the fractionated culture supernatant was measured by the ELISA method. The results are illustrated in FIGS. 7 and 8 to 13.

The results on the amount of GFAP in the culture supernatant in FIG. 7 and the histological evaluation in FIGS. 8 to 13 showed that GFAP was detected in the culture supernatant in all the cases of the auricular chondrocytes, and cartilage formation was observed by transplantation into nude mice. On the other hand, GFAP was not detected in all of the fibroblast cells and no formation of cartilage was observed.

FIGS. 7 to 13 showed that, in the case of the cultured human auricular chondrocytes which formed cartilage after transplantation and exhibited strong cartilage regeneration, the amount of GFAP in the culture supernatant was at least 0.05 ng/mL or more. These results suggested that if the GFAP content of the culture supernatant is 0.05 ng/mL or more, cultured human auricular chondrocytes to form the regenerated cartilage are contained. It was found that the value of the GFAP content of the culture supernatant can be used as a standard of the quality of regenerated cartilage.

Example 2

A regenerated cartilage was produced in accordance with the following procedures. FIG. 14 is a view schematically illustrating a process of producing the regenerated cartilage.

A portion of auricular cartilage (about 1 cm×5 mm×2 mm) was collected from patients. The chondrocytes were isolated by collagenase treatment.

The isolated chondrocytes were cultured in a DMEM/F12 culture solution containing 5% autoserum, FGF-2, and insulin for about three to six weeks. After culture, the cells increased by about 1000-fold in number of cells were harvested. The harvested cultured chondrocytes were injected into a PLLA scaffold material to form regenerated cartilage (FIG. 14).

At 39 days after culture (3 days before transplantation), the ELISA method was used to test the culture solution and the protein concentration of GFAP contained in the culture supernatant was measured. It was determined that when the GFAP content of the culture supernatant is confirmed to be 0.05 ng/mL or more at 39 days after culture (3 days before transplantation), the cells can be safely transplanted, can form cartilage in the body after transplantation, and can engraft as regenerated cartilage in living body.

What is claimed is:

1. A method for producing a regenerated cartilage comprising:
    allowing a group of cells containing auricular chondrocytes to stand in the presence of a culture medium;
    subsequently collecting at least a portion of a liquid component from the culture medium;
    measuring glial fibrillary acidic protein (GFAP) content of the collected liquid component;
    determining whether a regenerated cartilage can be obtained from the group of cells is suitable for transplantation wherein the cartilage is suitable for transplantation when the GFAP content is at least 0.05 ng per 1 ml of the liquid component; and
    forming regenerated cartilage from the group of cells.

2. The method for producing a regenerated cartilage according to claim 1, wherein forming the regenerated cartilage comprises three-dimensionally culturing chondrocytes using a scaffold material.

3. The method for producing regenerated cartilage according to claim 1, wherein the cartilage is suitable for transplantation when the GFAP content is 0.5 ng or more per 1 mL of the liquid component.

4. The method for producing regenerated cartilage according to claim 1, wherein the cartilage is suitable for transplantation when the GFAP content is 5 ng or more per 1 mL of the liquid component.

5. A method for producing a regenerated cartilage comprising:
    culturing auricular chondrocytes in a culture medium;
    collecting at least a portion of a liquid component from the culture medium;
    measuring glial fibrillary acidic protein (GFAP) content of the collected liquid component;
    selecting the cultured auricular chondrocytes having a GFAP content of at least 0.05 ng per 1 ml of the liquid component; and forming regenerated cartilage from the selected auricular chondrocytes.

6. The method according to claim 5, comprising selecting the cultured auricular chondrocytes having a GFAP content of at least 0.5 ng per 1 ml of the liquid component.

7. The method according to claim 5, comprising selecting the cultured auricular chondrocytes having a GFAP content of at least 5 ng per 1 ml of the liquid component.

8. The method according to claim 5, wherein forming the regenerated cartilage comprises three-dimensionally culturing chondrocytes using a scaffold material.

* * * * *